US00PP10754P

United States Patent [19]

VandenBerg

[11] Patent Number: Plant 10,754

[45] Date of Patent: Jan. 12, 1999

[54] CHRYSANTHEMUM PLANT NAMED 'ORANGE SUERTE'

[75] Inventor: Cornelis P. VandenBerg, Salinas, Calif.

[73] Assignee: Yoder Brothers, Inc., Barberton, Ohio

[21] Appl. No.: 867,697

[22] Filed: Jun. 2, 1997

[51] Int. Cl.[6] ..... A01H 5/00

[52] U.S. Cl. ..... Plt./82.3

[58] Field of Search ..... Plt./82.3, 74.1

[56] References Cited

U.S. PATENT DOCUMENTS

| | | | |
|---|---|---|---|
| P.P. 10,225 | 3/1998 | VandenBerg | Plt./74.1 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum* morifolium", Euphytica 29:525–530.

Gosling, ed., 1979, "the Chrysanthemum Manual–6$^{th}$ edition", the National Chrysanthemum Society, London, Essex Telegraph Press, Ltd., pp. 329–336.

Broerjes, et al., 1978, "Application of Mutation Breeding Methods In the Improvement of Vegetatively Propagated Crops", Elsevier Sci. Pub. Co., New York, pp. 162–175.

Searle, et al. 1968 "Chrysanthemums the Year Round", Blanford Press, London, pp. 27–29, 320–327.

Chan, 1966, "Chrysanthemum and nose mutations induced by x–rays", Am.Soc.Hort.Sci.Proc., pp. 613–620.

Broertjes, 1966, "Muatation breeding of chrysanthemums", Euphytica, 15:156–162.

Dowrick, et al., 1966 "The induction of mutations in Chrysanthemum using x–and gamma radiation", Euphytica, 15:204–210.

*Primary Examiner*—Howard J. Locker
*Attorney, Agent, or Firm*—C. A. Whealy

[57] ABSTRACT

A distinct cultivar of Chrysanthemum plant named 'Orange Suerte', characterized by its daisy-type inflorescences that are about 10 cm in diameter; attractive bright orange ray florets and bright yellow disc florets; numerous ray florets per inflorescence arranged in multiple rows; numerous disc florets per inflorescence; and excellent postproduction longevity with flowering stems maintaining good substance and color for about three to four weeks in an interior environment after one week of cool storage.

3 Drawing Sheets

The present invention relates to a new and distinct cultivar of Chrysanthemum plant, botanically known as *Dendranthema grandiflora* and referred to by the cultivair name 'Orange Suerte.'

The new cultivar is a product of a mutation induction breeding program conducted by the inventor in Fort Myers, Fla., and Salinas, Calif. The objective of the program is to create new Chrysanthemum cultivars having inflorescences with desirable form and floret colors, good substance, and excellent post-production longevity.

The new cultivar originated by exposing unrooted cuttings of the Chrysanthemum cultivar Suerte (disclosed in U.S. Plant Pat. No. 10,225) to a X-ray radiation level of 1,500 rads on Oct. 27, 1994 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar 'Orange Suerte' was discovered and initially selected by the inventor as a single flowering plant within this population on Apr. 20, 1995 and was re-selected on Dec. 12, 1995 during the first flowering of the initial selection. The selection of these plants was based on their desirable inflorescence form and floret colors, good substance, and excellent post-production longevity. In side-by-side comparisons conducted in Salinas, Calif., plants of the new Chrysanthemum differ from plants of the parent cultivar, 'Suerte', in ray floret color as plants of 'Suerte' have dark pink/purple-colored ray florets. However plants of the new Chrysanthemum are not significantly different from plants of 'Suerte' in any other horticultural characteristics. In side- by-side comparisions conducted in Salinas, Calif., plants of the new Chrysanthemum have also been compared to other similar cultivars such as 'Regal Suerte' (disclosed in U.S. Plant patent application Ser. No. 08,867,698) and 'Coral Suerte' (disclosed in U.S. Plant patent application Ser. No. 08/867,696). Plants of these cultivars also differ from plants of the new Chrysanthemum in ray floret color as plants of 'Regal Suerte' have dark purple-colored ray florets and plants of 'Coral Suerte' have coral-colored ray florets. Plants of the new Chrysanthemum are not significantly different from plants of 'Regal Suerte' in any other horticultural characteristics.

Asexual reproduction of the new cultivar by terminal cuttings taken in a controlled environment in Salinas, Calif., has shown that the unique features of this new Chrysanthemum are stable and reproduced true to type in successive generations.

The cultivar 'Orange Suerte' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Orange Suerte'. These characteristics in combination distinguish 'Orange Suerte' as a new and distinct cultivar:

1. Daisy-type inflorescences that are about 10 cm in diameter.
2. Attractive bright orange ray florets and bright yellow disc florets.
3. Numerous ray florets per inflorescence arranged in multiple rows.
4. Numerous disc florets per inflorescence.
5. Excellent postproduction longevity with flowering stems maintaining good substance and color for about three to four weeks in an interior environment after one week of cool storage.

The accompanying colored photographs illustrate the overall appearance of the new cultivar, showing the colors as true as it is reasonably possible to obtain in colored reproductions of this type.

The first photograph comprises a side perspective view of a typical flowering stem of 'Orange Suerte' grown as a single-stem spray cut Chrysanthemum.

The second photograph comprises a side perspective view of typical inflorescences of the cultivar 'Orange Suerte'.

The third photograph comprises a top perspective view of upper (top) and lower (bottom) surfaces of typical inflorescences of the cultivars Suerte (left) and 'Orange Suerte' (right) which shows the difference in ray floret colors.

The fourth photograph comprises a top perspective view of the upper surfaces of typical leaves of the cultivar 'Orange Suerte' at two different stages of development.

Floret and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse. Day and night temperatures ranged from 18° to 24° C. and 16° to 17° C., respectively, and light levels ranged from 2,500 to 3,500 foot-candles. Rooted cuttings were planted Feb. 13, 1997 and cut flowers were harvested on Apr. 21, 1997. After planting rooted cuttings of the new cultivar, plants received two weeks of long day/short nights following by short day/long nights until flowering. Plants were grown as single-stem, that is, without pinching. Measurements and numerical values represent averages for six typical flowering stems.

Botanial classification: *Dendranthema grandiflora* cultivar 'Orange Suerte'.

Commercial classification: Daisy spray-type cut Chrysanthemum.

Parentage: Induced mutation of *Dendranthema grandiflora* cultivar 'Suerte' (U.S. Plant Pat. No. 10,225).

Propagation:

*Type*.—Terminal tip cuttings.

*Time to rooting*.—Seven to ten days with soil tempeatures of 21C.

*Rooting habit*.—Fine, fibrous and well-branched.

Plant description:

*Appearance*.—Perennial herbaceous daisy spray-type cut flower. Stems upright, uniform habit and freely branching.

*Flowering stem length*.—About 94 cm.

*Foliage description*.—Leaf arrangement: Alternate. Leaf size, fully expanded: Length: About 10.5 cm. Width: About 7.5 cm. Leaf apex: Cuspidate. Leaf base: Attenuate. Leaf margin: Deeply lobed. Leaf texture: upper and lower surfaces slightly pubescent. Veins prominent on lower surface. Color: Young foliage upper surface: 147A. Young foliage lower surface: 147B. Mature foliage upper surface: 147A. Mature foliage lower surface: 147B. Venation upper surface: 147B. Venation lower surface: 147B. Petiole: Length: About 2.5 cm. Color: 147B.

Flowering description:

*Appearance*.—Daisy-type inflorescence form. Inflorescences borne on terminals, arising from leaf axils. Disc and ray florets arranged acropetally on receptacle.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 52 days later.

*Postproduction longevity*.—In an interior environment, flowering stems will maintain good color and substance for about three or four weeks in an interior environment after one week of cool storage.

*Quantity of inflorescences*.—About 11 inflorescences per flowering stem.

*Inflorescence size*.—Diameter: About 10 cm. Depth (height): About 1.2 cm. Diameter of disc: About 1.75 cm. Diameter of receptacle: About 7 mm.

*Ray florets*.—Shape: Oblong. Size: Length: About 4.6 cm. Width: About 1.1 cm. Apex: Rounded to dentate. Base: Attenuate. Margin: Entire. Texture: Satiny, smooth, glabrous Aspect: Flat. Number of ray florets per inflorescence: About 83. Color: When opening: Upper surface: 169A. Lower surface: 168D with red overtones. Base: 154A. Mature: Upper surface: 169A/169B. Lower surface: 168D with red overtones. Base: 154A.

*Disc florets*.—Shape: Tubular. Size: Length: About 7 mm. Width: Apex: About 2.5 mm. Base: About 1 mm. Number of disc florets per inflorescence: About 121. Color: Immature: 154A. Mature: Apex: 9A. Base: Greenish white. Throat: 9A.

*Peduncle*.—Aspect: Strong and angled about 50° to the stem. Length: First peduncle: About 10.5 cm. Fourth peduncle: About 16 cm. Seventh peduncle: About 22.5 cm. Texture: Pubescent. Color: 147B.

*Reproductive organs*.—Androecium: Present on disc florets only. Anther color: 15A. Pollen: Moderate, 15A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Orange Suerte', as illustrated and described.

* * * * *

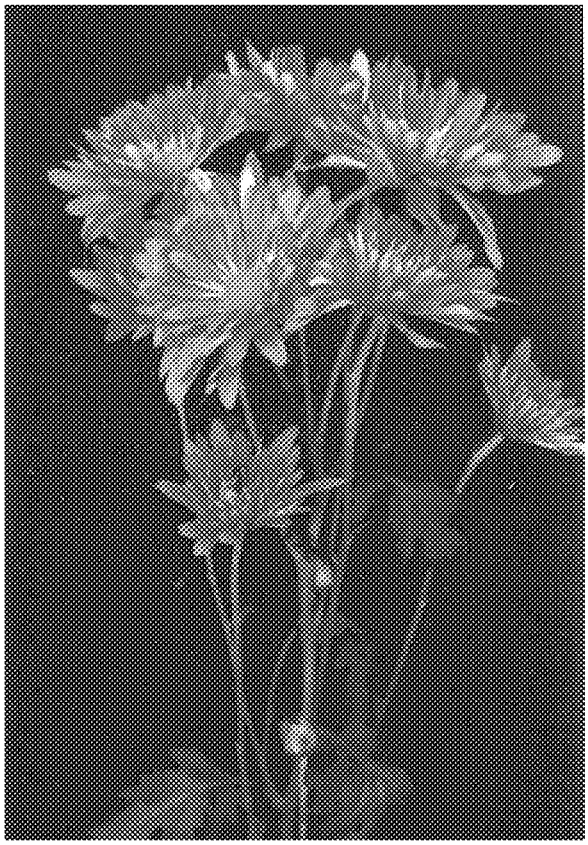

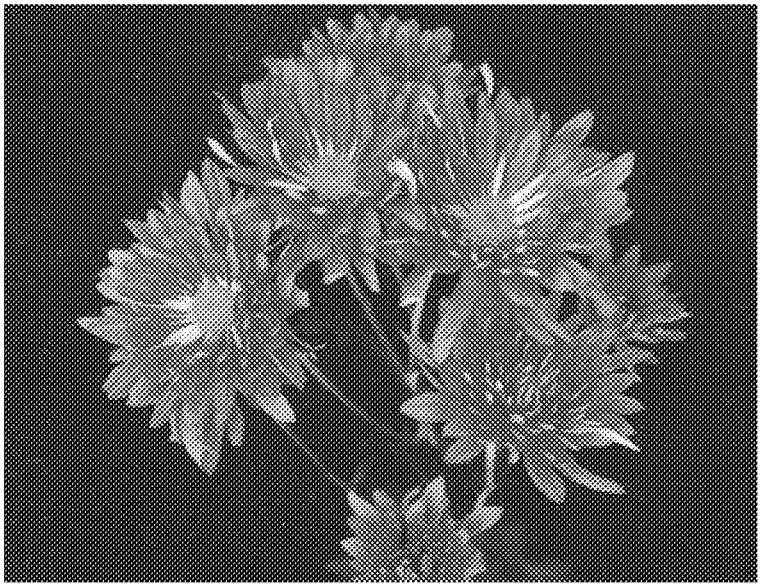

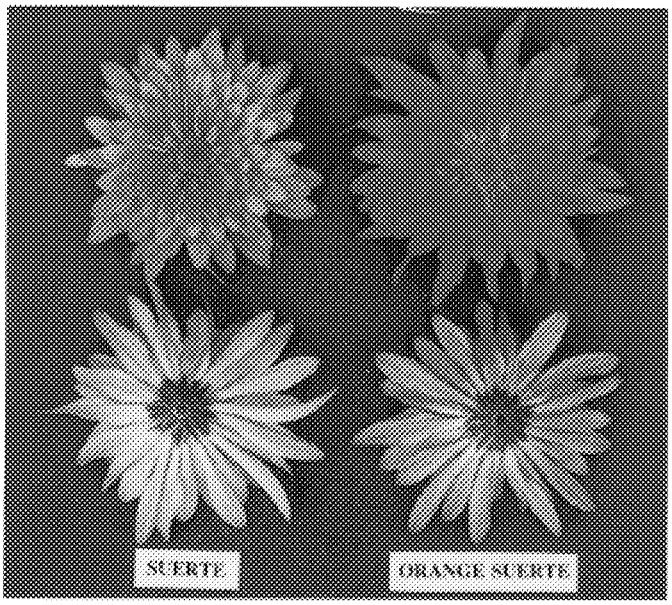
SUERTE
ORANGE SUERTE
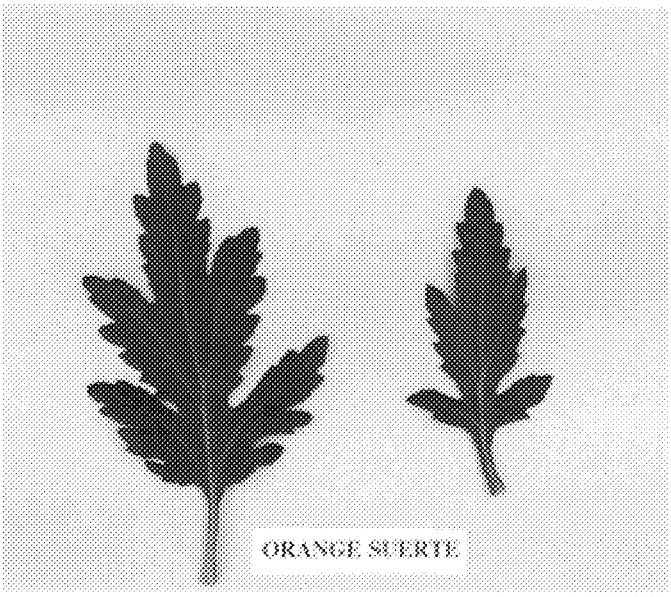
ORANGE SUERTE